(12) United States Patent
Nelson et al.

(10) Patent No.: US 8,022,023 B2
(45) Date of Patent: *Sep. 20, 2011

(54) LUBRICATING OIL ADDITIVE AND LUBRICATING OIL COMPOSITION CONTAINING SAME

(75) Inventors: Kenneth D. Nelson, Napa, CA (US); Edward A. Chiverton, Tenby (GB)

(73) Assignee: Chevron Oronite Company LLC, San Ramon, CA (US)

(*) Notice: Subject to any disclaimer, the term of this patent is extended or adjusted under 35 U.S.C. 154(b) by 224 days.

This patent is subject to a terminal disclaimer.

(21) Appl. No.: 12/215,739

(22) Filed: Jun. 30, 2008

(65) Prior Publication Data
US 2009/0325833 A1 Dec. 31, 2009

(51) Int. Cl.
*C10M 159/18* (2006.01)

(52) U.S. Cl. ........ 508/230; 508/287; 508/290; 508/291; 508/293

(58) Field of Classification Search .................. 508/230, 508/291, 292, 293, 289, 290
See application file for complete search history.

(56) References Cited

U.S. PATENT DOCUMENTS

| | | | |
|---|---|---|---|
| 4,259,194 A | 3/1981 | de Vries et al. | |
| 4,259,195 A | 3/1981 | King et al. | |
| 4,263,152 A | 4/1981 | King et al. | |
| 4,265,773 A | 5/1981 | de Vries et al. | |
| 4,272,387 A | 6/1981 | King et al. | |
| 4,283,295 A | 8/1981 | de Vries et al. | |
| 4,285,822 A | 8/1981 | de Vries et al. | |
| 4,324,672 A | 4/1982 | Levine et al. | |
| 4,357,149 A | 11/1982 | West et al. | |
| 4,500,439 A | 2/1985 | West et al. | |
| 6,372,696 B1 | 4/2002 | Tipton | |
| 6,962,896 B2 | 11/2005 | Ruhe, Jr. et al. | |
| 2005/0209111 A1 | 9/2005 | Ruhe, Jr. et al. | |

FOREIGN PATENT DOCUMENTS

| | | |
|---|---|---|
| GB | 1085903 | 10/1967 |
| RU | 2201433 | 3/2003 |

OTHER PUBLICATIONS

Yamaguchi et al. in *Tribology Transactions*, vol. 42 (4), pp. 895-901 (1999).

*Primary Examiner* — Ellen McAvoy
*Assistant Examiner* — Taiwo Oladapo

(57) ABSTRACT

A molybdated succinimide complex is disclosed which is prepared by a process comprising (a) reacting a succinimide of a polyamine of formula I:

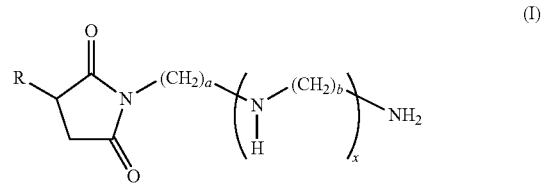

wherein R is a hydrocarbon radical having a number average molecular weight of about 500 to about 5,000, a and b are independently 2 or 3, and x is 0 to 10, with an ethylenically unsaturated carboxylic acid or anhydride thereof, in a charge mole ratio of the ethylenically unsaturated carboxylic acid or anhydride thereof to the succinimide of formula I of about 0.9:1 to about 1.05:1; and (b) reacting the succinimide product of step (a) with an acidic molybdenum compound. Also disclosed is a lubricating oil composition containing at least (a) a major amount of a base oil of lubricating viscosity and (b) a minor amount of the molybdated succinimide complex.

48 Claims, No Drawings

LUBRICATING OIL ADDITIVE AND LUBRICATING OIL COMPOSITION CONTAINING SAME

BACKGROUND OF THE INVENTION

1. Technical Field

The present invention generally relates to a lubricating oil additive and lubricating oil composition containing same.

2. Description of the Related Art

In general, organic molybdenum compounds are known to improve the lubricating properties of engine oils. For example, molybdenum dithiocarbamates are typically employed for the reduction of friction. The molybdenum dithiocarbamates, however, contain sulfur and slowly lose the ability to reduce friction unless an alternate sulfur source is present in the lubricating oil. Another example of organic molybdenum compounds are sulfurized molybdenum polyisobutenyl succinimide complexes which are used to mediate wear, reduce friction, and/or control oxidation. See, e.g., U.S. Pat. Nos. 4,259,194; 4,265,773; 4,283,295; 4,285,822; and 6,962,896 and U.S. Patent Application Publication No. 2005/0209111. Problems associated with the use of sulfur in a lubricating oil are that sulfur can be incompatible with emission control devices and can result in corrosion problems.

U.S. Pat. Nos. 4,357,149 and 4,500,439 disclose molybdated $C_{15}$-$C_{20}$ alkenyl succinimides. In Example XI of both of these patents, a molybdated succinimide is prepared by reacting a $C_{15}$-$C_{20}$ alkenyl succinic anhydride with triethylene tetramine followed by treatment with a molybdic acid solution.

Russian Patent No. 2201433 discloses a molybdated succinimide post-treated with maleic anhydride as an additive for motor oils used in internal combustion engines. Russian Patent No. 2201433 further discloses that the additives are prepared by reacting an alkenyl succinimide of polyethylene polyamine with ammonium molybdate in the presence of water as a promoter and then reacting the resulting product with maleic anhydride taken in amounts of 0.2 to 1.0 mole per 1 mole of alkenyl succinimide of polyethylene polyamine. All of the examples disclosed in Russian Patent No. 2201433 employ a high molecular weight polyisobutenyl (950 M.W.) succinic anhydride (PIBSA) in preparing the alkenyl succinimide of polyethylene polyamine.

Accordingly, it would be desirable to develop improved molybdenum-containing lubricating oil compositions which exhibit improved friction reduction, and wear and oxidation inhibition.

SUMMARY OF THE INVENTION

In accordance with one embodiment of the present invention, a molybdated succinimide complex prepared by a process which comprises (a) reacting a succinimide of a polyamine of formula I:

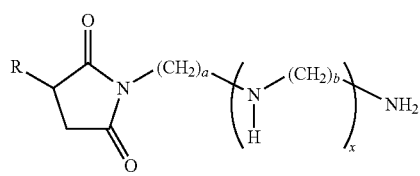

(I)

wherein R is a hydrocarbon radical having a number average molecular weight of about 500 to about 5,000, a and b are independently 2 or 3, and x is 0 to 10, with an ethylenically unsaturated carboxylic acid or anhydride thereof, in a charge mole ratio of the ethylenically unsaturated carboxylic acid or anhydride thereof to the succinimide of formula I of about 0.9:1 to about 1.05:1; and (b) reacting the succinimide product of step (a) with an acidic molybdenum compound.

In accordance with a second embodiment of the present invention, a process for preparing a molybdated succinimide complex is provided which comprises (a) reacting a succinimide of a polyamine of formula I:

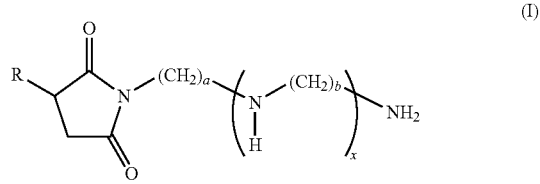

(I)

wherein R, a, b and x have the aforestated meanings, with an ethylenically unsaturated carboxylic acid or anhydride thereof, in a charge mole ratio of the ethylenically unsaturated carboxylic acid or anhydride thereof to the succinimide of formula I of about 0.9:1 to about 1.05:1; and (b) reacting the succinimide product of step (a) with an acidic molybdenum compound.

In accordance with a third embodiment of the present invention, a lubricating oil composition is provided which comprises (a) a major amount of a base oil of lubricating viscosity; and (b) a minor amount of a molybdated succinimide complex prepared by a process which comprises (i) reacting a succinimide of a polyamine of formula I:

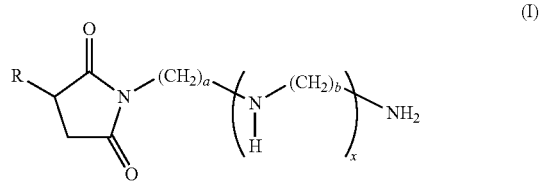

(I)

wherein R, a, b and x have the aforestated meanings, with an ethylenically unsaturated carboxylic acid or anhydride thereof, in a charge mole ratio of the ethylenically unsaturated carboxylic acid or anhydride thereof to the succinimide of formula I of about 0.9:1 to about 1.05:1; and (ii) reacting the succinimide product of step (i) with an acidic molybdenum compound.

In accordance with a fourth embodiment of the present invention, there is provided a method of operating an internal combustion engine which comprises operating the internal combustion engine with a lubricating oil composition comprising (a) a major amount of a base oil of lubricating viscosity and (b) a minor amount of a molybdated succinimide complex prepared by a process which comprises (i) reacting a succinimide of a polyamine of formula I:

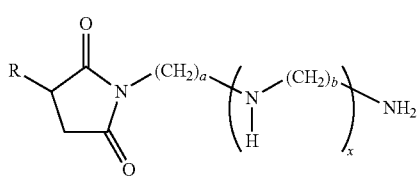

wherein R, a, b and x have the aforestated meanings, with an ethylenically unsaturated carboxylic acid or anhydride thereof, in a charge mole ratio of the ethylenically unsaturated carboxylic acid or anhydride thereof to the succinimide of formula I of about 0.9:1 to about 1.05:1; and (ii) reacting the succinimide product of step (i) with an acidic molybdenum compound.

In accordance with a fifth embodiment of the present invention, an additive package composition or concentrate is provided comprising (a) about 20 to about 80 weight percent of an inert organic diluent and (b) one or more of a molybdated succinimide complex prepared by a process which comprises (i) reacting a succinimide of a polyamine of formula I:

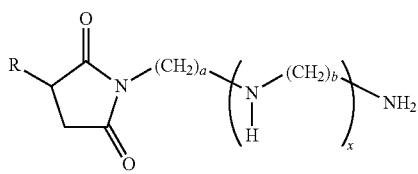

wherein R, a, b and x have the aforestated meanings, with an ethylenically unsaturated carboxylic acid or anhydride thereof, in a charge mole ratio of the ethylenically unsaturated carboxylic acid or anhydride thereof to the succinimide of formula I of about 0.9:1 to about 1.05:1; and (ii) reacting the succinimide product of step (i) with an acidic molybdenum compound.

The molybdated succinimide complex of the present invention advantageously provides high friction reduction, and wear and oxidation-corrosion inhibition when incorporated into a lubricating oil composition and used in an internal combustion engine.

DETAILED DESCRIPTION OF THE PREFERRED EMBODIMENTS

In general, a molybdated succinimide complex of the present invention is prepared by a process which involves at least (a) reacting a succinimide of a polyamine of formula I:

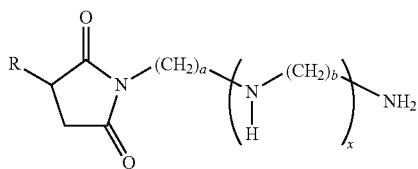

wherein R is a hydrocarbon radical having a number average molecular weight of about 500 to about 5,000, preferably a number average molecular weight of about 700 to about 2,500 and more preferably a number average molecular weight of about 710 to about 1,100; a and b are independently 2 or 3; and x is 0 to 10, preferably 1 to 6 and more preferably 2 to 5, with an ethylenically unsaturated carboxylic acid or anhydride thereof, in a charge mole ratio of the ethylenically unsaturated carboxylic acid or anhydride thereof to the succinimide of formula I of about 0.9:1 to about 1.05:1; and (b) reacting the succinimide product of step (a) with an acidic molybdenum compound. In one embodiment, R is an alkyl or alkenyl group. In another embodiment, R is a polyalkenyl group. A preferred polyalkenyl group is a polyisobutenyl group.

In step (a), a succinimide of formula I:

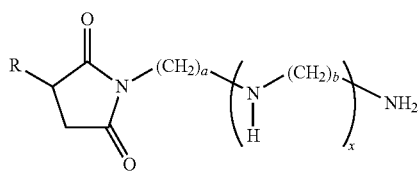

wherein R, a, b and x have the aforestated meanings, is reacted with an ethylenically unsaturated carboxylic acid in a charge mole ratio of the ethylenically unsaturated carboxylic acid or anhydride thereof to the succinimide of formula I of about 0.9:1 to about 1.05:1. The starting succinimide of formula I can be obtained by reacting an anhydride of formula II:

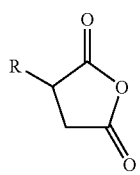

wherein R has the aforestated meaning with a polyamine. The anhydride of formula II is either commercially available from such sources as, for example, Sigma Aldrich Corporation (St. Louis, Mo., U.S.A.), or can be prepared by any method well known in the art.

Suitable polyamines for use in preparing the succinimide of formula I are polyalkylene polyamines, including polyalkylene diamines. Such polyalkylene polyamines will typically contain about 2 to about 12 nitrogen atoms and about 2 to 24 carbon atoms. Particularly suitable polyalkylene polyamines are those having the formula: $H_2N-(R^1NH)_c-H$ wherein $R^1$ is a straight- or branched-chain alkylene group having 2 or 3 carbon atoms and c is 1 to 9. Representative examples of suitable polyalkylene polyamines include ethylenediamine, diethylenetriamine, triethylenetetraamine, tetraethylenepentamine and mixtures thereof. Most preferably, the polyalkylene polyamine is tetraethylenepentamine.

Many of the polyamines suitable for use in the present invention are commercially available and others may be prepared by methods which are well known in the art. For example, methods for preparing amines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99 116.

Generally, the anhydride of formula II is reacted with the polyamine at a temperature of about 130° C. to about 220° C. and preferably from about 145° C. to about 175° C. The reaction can be carried out under an inert atmosphere, such as nitrogen or argon. The amount of anhydride of formula II employed in the reaction can range from about 30 to about 95 wt. % and preferably from about 40 to about 60 wt. %, based on the total weight of the reaction mixture.

Suitable ethylenically unsaturated carboxylic acids or their anhydrides include ethylenically unsaturated monocarboxylic acids or their anhydrides, ethylenically unsaturated dicarboxylic acids or their anhydrides and the like and mixtures thereof. Useful monocarboxylic acids or their anhydrides include, but are not limited to, acrylic acid, methacrylic acid, and the like and mixtures thereof. Useful ethylenically unsaturated dicarboxylic acids or their anhydrides include, but are not limited to, fumaric acid, maleic anhydride, mesaconic acid, citraconic acid, citraconic anhydride, itaconic acid, itaconic anhydride, and the like and mixtures thereof. A preferred ethylenically unsaturated carboxylic acid or anhydride thereof is maleic anhydride or a derivative thereof. This and similar anhydrides bond onto the succinimide starting compound to provide a carboxylic acid functionality. The treatment of the succinimide of formula I with the ethylenically unsaturated carboxylic acid or anhydrides thereof advantageously allows for a sufficient amount of the molybdenum compound to be incorporated into the complex.

Generally, the ethylenically unsaturated carboxylic acid or its anhydride is heated to a molten condition at a temperature in the range of from about 50° C. to about 100° C. and is thereafter mixed with the succinimide of formula I.

The molybdenum compounds used to prepare the molybdated succinimide complex of the present invention are acidic molybdenum compounds or salts of acidic molybdenum compounds. Generally, these molybdenum compounds are hexavalent. Representative examples of suitable molybdenum compounds include, but are not limited to, molybdenum oxide, molybdenum trioxide, molybdic acid, ammonium molybdate, sodium molybdate, potassium molybdate and other alkaline metal molybdates and other molybdenum salts such as hydrogen salts, e.g., hydrogen sodium molybdate, $MoOCl_4$, $MoO_2Br_2$, $Mo_2O_3Cl_6$, or similar acidic molybdenum compounds. Preferred acidic molybdenum compounds are molybdenum trioxide, molybdic acid, ammonium molybdate, and alkali metal molybdates. Particularly preferred is molybdenum trioxide.

In step (b), a mixture of the succinimide product of step (a) and acidic molybdenum compound is prepared with or without a diluent. A diluent is used, if necessary, to provide a suitable viscosity for easy stirring. Suitable diluents are lubricating oils and liquid compounds containing only carbon and hydrogen. If desired, ammonium hydroxide may also be added to the reaction mixture to provide a solution of ammonium molybdate Generally, the reaction mixture is heated at a temperature less than or equal to about 100° C. and preferably from about 80° C. to about 100° C. until the molybdenum is sufficiently reacted. The reaction time for this step is typically in the range of from about 15 minutes to about 5 hours and preferably from about 1 to about 2 hours. The molar ratio of the molybdenum compound to the succinimide product of step (a) is about 0.1:1 to about 2:1, preferably from about 0.5:1 to about 1.5:1 and most preferably about 1:1. Any water present following the reaction of the molybdenum compound and succinimide product of step (a) can be removed by heating the reaction mixture to a temperature greater than about 100° C., and preferably from about 120° C. to about 160° C.

Another embodiment of the present invention is directed to a lubricating oil composition containing at least (a) a major amount of a base oil of lubricating viscosity; and (b) a minor amount of the molybdated succinimide complex of this invention which is useful as a lubricating oil additive. The lubricating oil compositions can be prepared by admixing, by conventional techniques, an appropriate amount of the lubricating oil additive of this invention with a base oil of lubricating viscosity. The selection of the particular base oil depends on the contemplated application of the lubricant and the presence of other additives. Generally, a minor amount of the molybdated succinimide complex of this invention will vary from about 0.001 to about 10% by weight and preferably from about 0.5 to about 2% by weight, based on the total weight of the lubricating oil composition.

The base oil of lubricating viscosity for use in the lubricating oil compositions of this invention is typically present in a major amount, e.g., an amount of greater than 50 wt. %, preferably greater than about 70 wt. %, more preferably from about 80 to about 99.5 wt. % and most preferably from about 85 to about 98 wt. %, based on the total weight of the composition. The expression "base oil" as used herein shall be understood to mean a base stock or blend of base stocks which is a lubricant component that is produced by a single manufacturer to the same specifications (independent of feed source or manufacturer's location); that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fischer- Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$ oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl) silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The lubricating oil compositions of the present invention may also contain other conventional additives for imparting auxiliary functions to give a finished lubricating oil composition in which these additives are dispersed or dissolved. For example, the lubricating oil compositions can be blended with antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. A variety of the additives are known and commercially available. These additives, or their analogous compounds, can be employed for the preparation of the lubricating oil compositions of the invention by the usual blending procedures.

Examples of antioxidants include, but are not limited to, aminic types, e.g., diphenylamine, phenyl-alpha-napthylamine, N,N-di(alkylphenyl) amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic) phenol; and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonoamides, and phosphoramides; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, may also be used.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain) alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine and the like and mixtures thereof.

Examples of antifoaming agents include, but are not limited to, polymers of alkyl methacrylate; polymers of dimethylsilicone and the like and mixtures thereof.

Each of the foregoing additives, when used, is used at a functionally effective amount to impart the desired properties to the lubricant. Thus, for example, if an additive is a friction modifier, a functionally effective amount of this friction modifier would be an amount sufficient to impart the desired friction modifying characteristics to the lubricant. Generally, the concentration of each of these additives, when used, ranges from about 0.001% to about 20% by weight, and in one embodiment about 0.01% to about 10% by weight based on the total weight of the lubricating oil composition.

The final application of the lubricating oil compositions of this invention may be, for example, in marine cylinder lubricants in crosshead diesel engines, crankcase lubricants in automobiles and railroads and the like, lubricants for heavy machinery such as steel mills and the like, or as greases for bearings and the like. Whether the lubricating oil composition is fluid or solid will ordinarily depend on whether a thickening agent is present. Typical thickening agents include polyurea acetates, lithium stearate and the like.

In another embodiment of the invention, the lubricating oil additive of the present invention may be provided as an additive package or concentrate in which the additive is incorporated into a substantially inert, normally liquid organic diluent such as, for example, mineral oil, naphtha, benzene, toluene or xylene to form an additive concentrate. These concentrates usually contain from about 20% to about 80% by weight of such diluent. Typically a neutral oil having a viscosity of about 4 to about 8.5 cSt at 100° C. and preferably about 4 to about 6 cSt at 100° C. will be used as the diluent, though synthetic oils, as well as other organic liquids which are compatible with the additives and finished lubricating oil can also be used. The additive package will also typically contain one or more of the various other additives, referred to above, in the desired amounts and ratios to facilitate direct combination with the requisite amount of base oil.

The following non-limiting examples are illustrative of the present invention.

Example 1

Into a 500 ml, 3-neck round bottom flask equipped with an overhead mechanical stirrer, water condenser with nitrogen line and Dean-Stark trap, temperature controller, heating mantle, and thermocouple was added 252 g of a polyisobutenyl succinic anhydride (PIBSA) having a 750 number average molecular weight (Mn) polyisobutenyl group and a saponification number (SAP) of 139 mgKOH/g. The mixture was heated to about 100° C. and 47.3 g of tetraethylenepentamine (TEPA; 0.8 mole equivalent to PIBSA) was charged drop wise into the mixture via an addition funnel. Slight foaming occurred during the initial charge stage. After the TEPA was charged, the temperature was increased to 165° C. over about 60 minutes and was then held at 165° C. overnight.

The material was cooled and 50.00 g (0.0426 mol) was transferred to a 250 ml three neck round bottom flask. The flask was heated at 100° C. for maleic anhydride addition. Next, 4.18 g of maleic anhydride (1 mole equivalent to TEPA) was added. The reactor temperature was increased to 160° C. over an hour and then held at this temperature overnight.

The mixture was cooled to 85° C. and then 49.4 g of toluene, 6.12 g of molybdenum trioxide (1 mole equivalent to TEPA), 5 g of distilled water, and 2 drops of foam inhibitor were added. The mixture was stirred and heated at 100° C. overnight. The product was then filtered through Celite 512 in a warmed Buchner funnel under vacuum. The filtrate was collected and concentrated using a rotary evaporator (full pump vacuum at a maximum temperature of 140° C.) to remove toluene and residual water. The product was a viscous brown oil and had the following properties:

Mo=2.35 wt. %
N=5.7 wt. %
Total Base Number=140 mg KOH/g

Example 2

A molybdated succinimide complex was prepared using the same general procedure and components outlined in Example 1 except that the PIBSA:TEPA charge molar ratio was 0.5:1. The molybdated succinimide complex had a molybdenum content of 1.02 wt.

Example 3

A molybdated succinimide complex was prepared using the same general procedure and components outlined in Example 1 except that the PIBSA had a 1000 Mn polyisobutenyl group and a SAP number of 120 mg KOH/g. The molybdated succinimide complex had a molybdenum content of 5.9 wt. %.

Example 4

A molybdated succinimide complex was prepared using the same general procedure and components outlined in Example 3 except that the PIBSA:TEPA charge molar ratio was 0.5:1. The molybdated succinimide complex had a molybdenum content of 0.4 wt.

Example 5

A molybdated succinimide complex was prepared using the same general procedure and components outlined in Example 1 except that the PIBSA had a 2300 Mn polyisobutenyl group and a SAP number of 56.4 mg KOH/g. The molybdated succinimide complex had a molybdenum content of 1.8 wt. %.

Example 6

A molybdated succinimide complex was prepared using the same general procedure and components outlined in Example 5 except that the PIBSA:TEPA charge molar ratio was 0.5:1. The molybdated succinimide complex had a molybdenum content of 0.6 wt.

Example 7

A molybdated succinimide complex was prepared using the same general procedure and components outlined in Example 3 except that the PIBSA:TEPA charge molar ratio was 1:1. The molybdated succinimide complex had a molybdenum content of 4.6 wt. %.

Comparative Example A

A baseline lubricating oil formulation was formed containing 3.8 wt. % succinimide dispersant, 3.5 mM/kg low overbased calcium sulfonate, 45 mM/kg highly overbased calcium sulfonate, 5 mM/kg zinc dithiophosphate derived from a secondary alcohol, 2 mM/kg zinc dithiophosphate from a primary alcohol, 0.5 wt. % diphenylamine anti-oxidant, 0.3 wt. % pour point depressant, 4.8 wt. % olefin copolymer viscosity index improver and 10 ppm foam inhibitor in a Group II base oil.

Comparative Example B

A baseline lubricating oil formulation was formed containing the same additives, base oil and treat rate as in Comparative Example A. A commercially available molybdenum oxide succinimide complex derived from a polyisobutenyl (1000 M.W.) was formulated into this baseline lubricating oil formulation such that the total Mo content in the formulation was 500 ppm.

Example 8

A baseline lubricating oil formulation was formed containing the same additives, base oil and treat rate as in Comparative Example A. The lubricating oil additive of Example 1 was formulated into this baseline lubricating oil formulation such that the total Mo content in the formulation was 500 ppm.

Example 9

A baseline lubricating oil formulation was formed containing the same additives, base oil and treat rate as in Comparative Example A. The lubricating oil additive of Example 2 was formulated into this baseline lubricating oil formulation such that the total Mo content in the formulation was 500 ppm.

Example 10

A baseline lubricating oil formulation was formed containing the same additives, base oil and treat rate as in Comparative Example A. The lubricating oil additive of Example 3 was formulated into this baseline lubricating oil formulation such that the total Mo content in the formulation was 500 ppm.

Example 11

A baseline lubricating oil formulation was formed containing the same additives, base oil and treat rate as in Comparative Example A. The lubricating oil additive of Example 4 was formulated into this baseline lubricating oil formulation such that the total Mo content in the formulation was 500 ppm.

Example 12

A baseline lubricating oil formulation was formed containing the same additives, base oil and treat rate as in Comparative Example A. The lubricating oil additive of Example 5 was formulated into this baseline lubricating oil formulation such that the total Mo content in the formulation was 500 ppm.

Example 13

A baseline lubricating oil formulation was formed containing the same additives, base oil and treat rate as in Comparative Example A. The lubricating oil additive of Example 6 was formulated into this baseline lubricating oil formulation such that the total Mo content in the formulation was 500 ppm.

Example 14

A baseline lubricating oil formulation was formed containing the same additives, base oil and treat rate as in Comparative Example A. The lubricating oil additive of Example 7 was formulated into this baseline lubricating oil formulation such that the total Mo content in the formulation was 500 ppm.

Oxidation Performance

The effect of oxidation on the lubricating oil compositions of Examples 8-14 containing the lubricating oil additive of the present invention were analyzed and compared to the effect of oxidation on the baseline lubricating oil formulation of Comparative Example A and the lubricating oil composition of Comparative Example B in an oxidation bench test. The oxidation studies were carried out in a bulk oil oxidation bench test as described by E. S. Yamaguchi et al. in *Tribology Transactions*, Vol 42 (4), 895-901 (1999). In this test, the rate of oxygen uptake at constant pressure by a given weight of oil at 170° C. was monitored. The time required to reach a period of rapid oxygen uptake, known as auto-oxidation, was designated as induction time. Bench test results are generally reproducible to within ±0.5 hours. In this test, the longer induction time corresponds to more effective antioxidant. The oxidation bench test results are presented in Table 1.

TABLE 1

Oxidation Bench Test Results

| Comp. Ex. Ex. | Mo Treat Rate | Induction Time |
|---|---|---|
| Comparative Ex. A | — | 15 |
| Comparative Ex. B | 500 ppm | 29 |
| Example 8 | 500 ppm | 55 |
| Example 9 | 500 ppm | 25 |
| Example 10 | 500 ppm | 27 |
| Example 11 | 500 ppm | 61 |
| Example 12 | 500 ppm | 30 |
| Example 13 | 500 ppm | 33 |
| Example 14 | 500 ppm | 24 |

As the data show, the lubricating oil compositions of this invention were comparable and, in some instances, significantly better than lubricating oil compositions outside the scope of this invention.

Comparative Example C

Into a 100 ml, round bottom flask equipped with a magnetic stirrer, water condenser with nitrogen line and Dean-Stark trap, temperature controller, heating mantle, and thermocouple was added 25.1 g of a commercially available molybdenum oxide treated mono-succinimide dispersant prepared from polyisobutenyl (1000 M.W.) succinic anhydride (PIBSA) and a polyamine with about five amine groups per molecule having 4.6% molybdenum and 2.2% nitrogen by weight. The charge mole ratio of polyamine:PIBSA was about 0.8:1. The molybdenum oxide treated mono-succinimide dispersant was stirred and heated to 110° C. while adding 1.68 g of maleic anhydride (1 mole equivalent). The mixture was stirred at about 160° C. for 1 hour to yield a black viscous oil.

Comparative Example D

Into a 100 ml, round bottom flask equipped with a magnetic stirrer, water condenser with nitrogen line and Dean-Stark trap, temperature controller, heating mantle, and thermocouple was added 25.1 g of a commercially available molybdenum oxide treated mono-succinimide dispersant prepared from polyisobutenyl (1000 M.W.) succinic anhydride (PIBSA) and a polyamine with about five amine groups per molecule having 4.6% molybdenum and 2.2% nitrogen by weight. The charge mole ratio of polyamine:PIBSA was about 0.8:1. The molybdenum oxide treated mono-succinimide dispersant was stirred and heated to 110° C. while adding 1.68 g of maleic anhydride (2 mole equivalents). The mixture was stirred at about 160° C. for 1 hour to yield a black viscous oil.

Comparative Example E

A baseline formulation was formed containing 5 wt. % succinimide dispersant, 3 wt. % borated succinimide dispersant, 4 mM/kg low overbased calcium sulfonate, 58 mM/kg carboxylate detergent, 8 mM/kg zinc dithiophosphate, 0.5 wt. % diphenylamine antioxidant, 0.5 wt. % hindered phenol anti-oxidant, 0.3 wt. % pour point depressant, 9.85 wt. % olefin copolymer viscosity index improver and 5 ppm foam inhibitor in a Group II base oil.

Comparative Example F

A baseline lubricating oil formulation was formed containing the same additives, base oil and treat rate as in Comparative Example E. A commercially available molybdenum oxide succinimide complex derived from a polyisobutenyl (1000 M.W.) was formulated into this baseline lubricating oil formulation such that the total Mo content in the formulation was 500 ppm.

Comparative Example G

A baseline lubricating oil formulation was formed containing the same additives, base oil and treat rate as in Comparative Example E. A commercially available molybdenum oxide succinimide complex derived from a polyisobutenyl (1000 M.W.) was formulated into this baseline lubricating oil formulation at 1 wt. %.

Comparative Example H

A baseline lubricating oil formulation was formed containing the same additives, base oil and treat rate as in Comparative Example E. The lubricating oil additive of Comparative Example C was formulated into this baseline lubricating oil formulation such that the total Mo content in the formulation was 500 ppm.

Comparative Example I

A baseline lubricating oil formulation was formed containing the same additives, base oil and treat rate as in Comparative Example E. The lubricating oil additive of Comparative Example C was formulated into this baseline lubricating oil formulation at 1 weight percent.

Comparative Example J

A baseline lubricating oil formulation was formed containing the same additives, base oil and treat rate as in Comparative Example E. The lubricating oil additive of Comparative Example D was formulated into this baseline lubricating oil formulation such that the total Mo content in the formulation was 500 ppm.

Comparative Example K

A baseline lubricating oil formulation was formed containing the same additives, base oil and treat rate as in Comparative Example E. The lubricating oil additive of Compara- Example D was formulated into this baseline lubricating oil formulation at 1 weight percent.

Example 15

A baseline lubricating oil formulation was formed containing the same additives, base oil and treat rate as in Comparative Example E. The lubricating oil additive of Example 1 was formulated into this baseline lubricating oil formulation at 500 ppm on a Mo basis.

Example 16

A baseline lubricating oil formulation was formed containing the same additives, base oil and treat rate as in Comparative Example E. The lubricating oil additive of Example 1 was formulated into this baseline lubricating oil formulation at 1 wt. %.

Example 17

A baseline lubricating oil formulation was formed containing the same additives, base oil and treat rate as in Comparative Example E. The lubricating oil additive of Example 2 was formulated into this baseline lubricating oil formulation such that the total Mo content in the formulation was 500 ppm.

Example 18

A baseline lubricating oil formulation was formed containing the same additives, base oil and treat rate as in Comparative Example E. The lubricating oil additive of Example 2 was formulated into this baseline lubricating oil formulation at 1 wt. %.

Example 19

A baseline lubricating oil formulation was formed containing the same additives, base oil and treat rate as in Comparative Example E. The lubricating oil additive of Example 3 was formulated into this baseline lubricating oil formulation such that the total Mo content in the formulation was 500 ppm.

Example 20

A baseline lubricating oil formulation was formed containing the same additives, base oil and treat rate as in Comparative Example E. The lubricating oil additive of Example 3 was formulated into this baseline lubricating oil formulation at 1 wt. %.

Example 21

A baseline lubricating oil formulation was formed containing the same additives, base oil and treat rate as in Comparative Example E. The lubricating oil additive of Example 4 was formulated into this baseline lubricating oil formulation such that the total Mo content in the formulation was 500 ppm.

Example 22

A baseline lubricating oil formulation was formed containing the same additives, base oil and treat rate as in Comparative Example E. The lubricating oil additive of Example 4 was formulated into this baseline lubricating oil formulation at 1 wt. %.

Example 23

A baseline lubricating oil formulation was formed containing the same additives, base oil and treat rate as in Comparative Example E. The lubricating oil additive of Example 5 was formulated into this baseline lubricating oil formulation such that the total Mo content in the formulation was 500 ppm.

Example 24

A baseline lubricating oil formulation was formed containing the same additives, base oil and treat rate as in Comparative Example E. The lubricating oil additive of Example 5 was formulated into this baseline lubricating oil formulation at 1 wt. %.

Example 25

A baseline lubricating oil formulation was formed containing the same additives, base oil and treat rate as in Comparative Example E. The lubricating oil additive of Example 6 was formulated into this baseline lubricating oil formulation such that the total Mo content in the formulation was 500 ppm.

Example 26

A baseline lubricating oil formulation was formed containing the same additives, base oil and treat rate as in Comparative Example E. The lubricating oil additive of Example 6 was formulated into this baseline lubricating oil formulation at 1 wt. %.

High Frequency Reciprocating Rig (HFRR) Evaluation

The HFRR wear and friction performance of the lubricating oil compositions of Examples 15-26 of the present invention were evaluated and compared to the baseline lubricating oil formulation of Comparative Example E and the lubricating oil compositions of Comparative Examples F-K. The HFRR test is an industry recognized bench test for determining the valve train wear performance in candidate lubricating oils. The PCS instrument uses an electromagnetic vibrator to oscillate a specimen (the ball) over a small amplitude while pressing against a fixed specimen (a flat disk). The amplitude and frequency of the oscillation and the load are variable. The frictional force between the ball and flat and the electrical contact resistance (ECR) are measured. The flat, stationary specimen is held in a bath to which the lubricating oil is added, and can be heated. The lubricating oils are pretreated with about 6% by weight, based on the total weight of lubricating oil, carbon black. The carbon black is stirred into the oil to wet it and then homogenized for 15 minutes prior to testing. The wear scars on the balls are measured manually on an optical microscope and recorded. In this test, a smaller wear scar corresponds to a more effective anti-wear agent and a smaller coefficient of friction corresponds to a more effective friction modifier. The HFRR wear and friction performance data are presented in Table 2.

TABLE 2

HFRR Wear and Friction Performance Results

| Comp. Ex./Ex. | Concentration | Coefficient of Friction | Wear Scar (μm) |
|---|---|---|---|
| Comparative Ex. E | — | 0.139 | 195 |
| Comparative Ex. F | 500 ppm | 0.124 | 171 |
| Comparative Ex. G | 1 wt. % | 0.130 | 195 |
| Comparative Ex. H | 500 ppm | 0.139 | 145 |

TABLE 2-continued

HFRR Wear and Friction Performance Results

| Comp. Ex./Ex. | Concentration | Coefficient of Friction | Wear Scar (μm) |
|---|---|---|---|
| Comparative Ex. I | 1 wt. % | 0.139 | 151 |
| Comparative Ex. J | 500 ppm | 0.132 | 149 |
| Comparative Ex. K | 1 wt. % | 0.138 | 146 |
| Example 15 | 500 ppm | 0.081 | 158 |
| Example 16 | 1 wt. % | 0.124 | 182 |
| Example 17 | 500 ppm | 0.133 | 195 |
| Example 18 | 1 wt. % | 0.136 | 211 |
| Example 19 | 500 ppm | 0.140 | 135 |
| Example 20 | 1 wt. % | 0.132 | 137 |
| Example 21 | 500 ppm | 0.113 | 191 |
| Example 22 | 1 wt. % | 0.137 | 193 |
| Example 23 | 500 ppm | 0.135 | 170 |
| Example 24 | 1 wt. % | 0.138 | 150 |
| Example 25 | 500 ppm | 0.132 | 196 |
| Example 26 | 1 wt. % | 0.138 | 173 |

As the data show, the lubricating oil compositions of this invention were comparable and, in some instances, significantly better than lubricating oil compositions outside the scope of this invention.

Comparative Example L

Into a 500 ml, 3-neck round bottom flask equipped with an overhead mechanical stirrer, water condenser with nitrogen line and Dean-Stark trap, temperature controller, heating mantle, and thermocouple was added 60.07 g of octadecenyl succinic anhydride (ODSA) (available from Sigma Aldrich Corporation, St. Louis, Mo., U.S.A.), 60.08 g of Exxon 150 neutral oil and three drops of foam inhibitor (200 to 350 cSt; available from Dow Corning). The mixture was heated to 100° C. and 32.88 g of tetraethylenepentamine (TEPA; 1.0 mole equivalent to ODSA) was charged drop wise into the mixture via an addition funnel. Slight foaming occurred during the initial charge stage. After the TEPA was charged, the temperature was increased to 160° C. over about 60 minutes and then held at 160° C. for three hours.

The material was cooled to less than 100° C. and 25.01 g of molybdenum trioxide (1 mole equivalent to TEPA), 69 g of toluene, 17 g of distilled water, and 0.1 g of foam inhibitor were added. The mixture was brought to 100° C. and under agitation a gel formed with evolution of foam. 116 g of Exxon 100N oil was added and the mixture was stirred overnight to yield a greenish brown gel. Accordingly, there was no attempt to react the gel with maleic anhydride.

Comparative Example M

Into a 500 ml, 3-neck round bottom flask equipped with an overhead mechanical stirrer, water condenser with nitrogen line and Dean-Stark trap, temperature controller, heating mantle, and thermocouple was added 60.6 g of a polyisobutenyl (1000 M.W.) succinic anhydride having a SAP number of 120.3 mgKOH/g. The mixture was heated to 100° C. and 10.45 g of tetraethylenepentamine (TEPA; 1.0 mole equivalent) was added. After the TEPA was charged, the temperature was increased to 180° C. over about 60 minutes and then held at 160° C. for one hour. After cooling overnight, 12.2 g of Exxon 100N oil was added to yield a viscous brown oil.

The material was heated to about 90° C. and 82 g of toluene was added to form a solution, followed by 7.9 g of molybdenum trioxide (1 mole equivalent to TEPA), and 8.3 g of distilled water. The mixture was stirred at 90° C. for 1.5 hours and then the temperature was raised to 160° C. and toluene and water were removed over about 4 hours. The product was a viscous brown oil. Next, 64 g of toluene was added and the mixture was heated to 95° C. to reduce the viscosity for filtration. Several attempts were made to filter the product through a Whatman brand #1 and #4 filter paper with and without diatomaceous earth filter aid without success. After repeated dilution of the product with Exxon 100N oil, the product could not be filtered. Accordingly, there was no attempt to react the product with maleic anhydride.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A molybdated succinimide complex prepared by a process which comprises (a) reacting a succinimide of a polyamine of formula I:

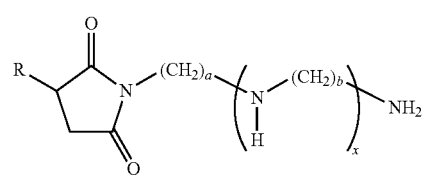

(I)

wherein R is a hydrocarbon radical having a number average molecular weight of about 500 to about 5,000, a and b are independently 2 or 3, and x is 0 to 10, with an ethylenically unsaturated carboxylic acid, in a charge mole ratio of the ethylenically unsaturated carboxylic acid to the succinimide of formula I of about 0.9:1 to about 1.05:1; and (b) reacting the succinimide product of step (a) with an acidic molybdenum compound.

2. The molybdated succinimide complex of claim 1, wherein R is a hydrocarbon radical having a number average molecular weight of about 700 to about 2,500.

3. The molybdated succinimide complex of claim 1, wherein R is a hydrocarbon radical having a number average molecular weight of about 710 to about 1,100.

4. The molybdated succinimide complex of claim 1, wherein R is a polyisobutenyl radical.

5. The molybdated succinimide complex of claim 1, wherein R is a polyisobutenyl radical having a number average molecular weight of about 700 to about 2,500.

6. The molybdated succinimide complex of claim 1, wherein R is a polyisobutenyl radical having a number average molecular weight of about 710 to about 1,100.

7. The molybdated succinimide complex of claim 1, wherein a and b are each 2, and x is 2 to 5.

8. The molybdated succinimide complex of claim 4, wherein a and b are each 2, and x is 2 to 5.

9. The molybdated succinimide complex of claim 1, wherein the ethylenically unsaturated carboxylic acid is an ethylenically unsaturated monocarboxylic acid.

10. The molybdated succinimide complex of claim 9, wherein the ethylenically unsaturated monocarboxylic acid is selected from the group consisting of acrylic acid, methacrylic acid and mixtures thereof.

11. The molybdated succinimide complex of claim 1, wherein the ethylenically unsaturated carboxylic acid is an ethylenically unsaturated dicarboxylic acid.

12. The molybdated succinimide complex of claim 11, wherein the ethylenically unsaturated dicarboxylic acid is selected from the group consisting of fumaric acid, mesaconic acid, citraconic acid, itaconic acid, and mixtures thereof.

13. The molybdated succinimide complex of claim 1, wherein the acidic molybdenum compound is selected from the group consisting of molybdenum oxide, molybdic acid, ammonium molybdate, sodium molybdate, potassium molybdates, hydrogen sodium molybdate, $MoOCl_4$, $MoO_2Br_2$, $Mo_2O_3Cl_6$, molybdenum trioxide and mixtures thereof.

14. The molybdated succinimide complex of claim 1, wherein the ethylenically unsaturated carboxylic acid is selected from the group consisting of acrylic acid, methacrylic acid and mixtures thereof and the acidic molybdenum compound is molybdenum trioxide.

15. The molybdated succinimide complex of claim 4, wherein the ethylenically unsaturated carboxylic acid is selected from the group consisting of acrylic acid, methacrylic acid and mixtures thereof and the acidic molybdenum compound is molybdenum trioxide.

16. The molybdated succinimide complex of claim 1, wherein the molar ratio of the molybdenum compound to the succinimide product of step (a) is about 0.1:1 to about 2:1.

17. The molybdated succinimide complex of claim 1, wherein the molar ratio of the molybdenum compound to the succinimide product of step (a) is about 0.5:1 to about 1.5:1.

18. A process for preparing a molybdated succinimide complex, the process comprising (a) reacting a succinimide of a polyamine of formula I:

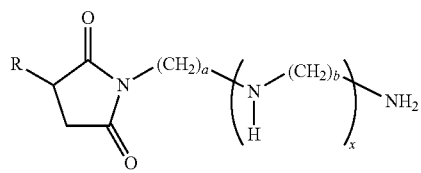

(I)

wherein R is a hydrocarbon radical having a number average molecular weight of about 500 to about 5,000, a and b are independently 2 or 3, and x is 0 to 10, with an ethylenically unsaturated carboxylic acid, in a charge mole ratio of the ethylenically unsaturated carboxylic acid to the succinimide of formula I of about 0.9:1 to about 1.05:1; and (b) reacting the succinimide product of step (a) with an acidic molybdenum compound.

19. The process of claim 18, wherein R is a hydrocarbon radical having a number average molecular weight of about 700 to about 2,500.

20. The process of claim 18, wherein R is a hydrocarbon radical having a number average molecular weight of about 710 to about 1,100.

21. The process of claim 18, wherein R is a polyisobutenyl radical.

22. The process of claim 18, wherein R is a polyisobutenyl radical having a number average molecular weight of about 700 to about 2,500.

23. The process of claim 18, wherein R is a polyisobutenyl radical having a number average molecular weight of about 710 to about 1,100.

24. The process of claim 18, wherein the ethylenically unsaturated carboxylic acid is an ethylenically unsaturated monocarboxylic acid.

25. The process of claim 24, wherein the ethylenically unsaturated monocarboxylic acid is selected from the group consisting of acrylic acid, methacrylic acid and mixtures thereof.

26. The process of claim 18, wherein the ethylenically unsaturated carboxylic acid is an ethylenically unsaturated dicarboxylic acid.

27. The process of claim 26, wherein the ethylenically unsaturated dicarboxylic acid is selected from the group consisting of fumaric acid, mesaconic acid, citraconic acid, itaconic acid, and mixtures thereof.

28. The process of claim 18, wherein the acidic molybdenum compound is selected from the group consisting of molybdenum oxide, molybdic acid, ammonium molybdate, sodium molybdate, potassium molybdates, hydrogen sodium molybdate, $MoOCl_4$, $MoO_2Br_2$, $Mo_2O_3Cl_6$, molybdenum trioxide and mixtures thereof.

29. The process of claim 18, wherein the ethylenically unsaturated carboxylic acid is selected from the group consisting of acrylic acid, methacrylic acid and mixtures thereof and the acidic molybdenum compound is molybdenum trioxide.

30. The process of claim 18, wherein the molar ratio of the molybdenum compound to the succinimide product of step (a) is about 0.1:1 to about 2:1.

31. The process of claim 18, wherein the molar ratio of the molybdenum compound to the succinimide product of step (a) is about 0.5:1 to about 1.5:1.

32. A lubricating oil composition comprising (a) a major amount of a base oil of lubricating viscosity; and (b) a minor amount of a molybdated succinimide complex prepared by a process which comprises (i) reacting a succinimide of a polyamine of formula I:

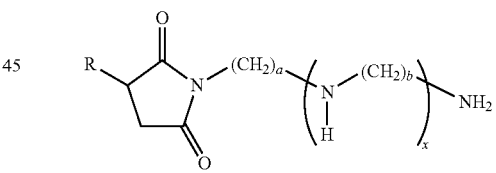

(I)

wherein R is a hydrocarbon radical having a number average molecular weight of about 500 to about 5,000, a and b are independently 2 or 3, and x is 0 to 10, with an ethylenically unsaturated carboxylic acid, in a charge mole ratio of the ethylenically unsaturated carboxylic acid to the succinimide of formula I of about 0.9:1 to about 1.05:1; and (ii) reacting the succinimide product of step (i) with an acidic molybdenum compound.

33. The lubricating oil composition of claim 32, wherein the base oil of lubricating viscosity is comprised of a mineral base oil.

34. The lubricating oil composition of claim 32, wherein R is a hydrocarbon radical having a number average molecular weight of about 700 to about 2,500.

35. The lubricating oil composition of claim 32, wherein R is a hydrocarbon radical having a number average molecular weight of about 710 to about 1,100.

36. The lubricating oil composition of claim 32, wherein R is a polyisobutenyl radical.

37. The lubricating oil composition of claim 32, wherein R is a polyisobutenyl radical having a number average molecular weight of about 700 to about 2,500.

38. The lubricating oil composition of claim 32, wherein R is a polyisobutenyl radical having a number average molecular weight of about 710 to about 1,100.

39. The lubricating oil composition of claim 32, wherein the ethylenically unsaturated carboxylic acid is selected from the group consisting of fumaric acid, mesaconic acid, citraconic acid, itaconic acid, and mixtures thereof.

40. The lubricating oil composition of claim 32, wherein the acidic molybdenum compound is selected from the group consisting of molybdenum oxide, molybdic acid, ammonium molybdate, sodium molybdate, potassium molybdates, hydrogen sodium molybdate, $MoOCl_4$, $MoO_2Br_2$, $Mo_2O_3Cl_6$, molybdenum trioxide and mixtures thereof.

41. The lubricating oil composition of claim 32, wherein the ethylenically unsaturated carboxylic acid selected from the group consisting of acrylic acid, methacrylic acid and mixtures thereof and the acidic molybdenum compound is molybdenum trioxide.

42. The lubricating oil composition of claim 32, wherein the minor amount of the molybdated alkenyl succinimide complex is about 0.001 wt. % to about 10 wt. %, based on the total weight of the composition.

43. The lubricating oil composition of claim 36, wherein the minor amount of the molybdated alkenyl succinimide complex is about 0.001 wt. % to about 10 wt. %, based on the total weight of the composition.

44. The lubricating oil composition of claim 32, further comprising at least one additive selected from the group consisting of metallic detergents, ashless dispersants, friction modifiers, extreme pressure agents, viscosity index improvers and pour point depressants.

45. The lubricating oil composition of claim 32, having a phosphorous content not exceeding 0.05 wt. %, based on the total weight of the composition.

46. The lubricating oil composition of claim 32, having a sulfur content not exceeding 0.4 wt. %, based on the total weight of the composition.

47. A method of operating an internal combustion engine comprising the step of operating the internal combustion engine with the lubricating oil composition of claim 32.

48. A method of operating an internal combustion engine comprising the step of operating the internal combustion engine with the lubricating oil composition of claim 43.

* * * * *